United States Patent
Schilling et al.

(10) Patent No.: US 11,606,963 B2
(45) Date of Patent: Mar. 21, 2023

(54) COMPOSITION CONTAINING GLYCOLIPIDS AND PRESERVATIVES

(71) Applicant: Evonik Operations GmbH, Essen (DE)

(72) Inventors: Martin Schilling, Bonn (DE); Josef Lorenz, Krefeld (DE); Kathrin Daniela Brandt, Düsseldorf (DE); Monica Desiree van Logchem, Zevenbergen (NL); Maciej Olek, Kahl (DE); Hans Henning Wenk, Mülheim an der Ruhr (DE)

(73) Assignee: Evonik Operations GmbH, Essen (DE)

( * ) Notice: Subject to any disclaimer, the term of this patent is extended or adjusted under 35 U.S.C. 154(b) by 324 days.

(21) Appl. No.: 16/332,979

(22) PCT Filed: Sep. 29, 2017

(86) PCT No.: PCT/EP2017/074795
§ 371 (c)(1),
(2) Date: Mar. 13, 2019

(87) PCT Pub. No.: WO2018/065314
PCT Pub. Date: Apr. 12, 2018

(65) Prior Publication Data
US 2019/0269158 A1    Sep. 5, 2019

(30) Foreign Application Priority Data
Oct. 7, 2016   (EP) .................................... 16192743

(51) Int. Cl.
*A23L 3/3517* (2006.01)
*A23L 3/3472* (2006.01)
(Continued)

(52) U.S. Cl.
CPC ............ *A23L 3/3517* (2013.01); *A01N 43/16* (2013.01); *A23L 3/349* (2013.01); *A23L 3/3472* (2013.01);
(Continued)

(58) Field of Classification Search
CPC ........ A23L 3/3517; A23L 27/86; A23L 29/03; A23L 3/3472; A23L 3/349; A23L 3/3508; A01N 43/16; A61K 8/36
(Continued)

(56) References Cited

U.S. PATENT DOCUMENTS

| 4,920,100 A | 4/1990 | Lehmann et al. |
| 5,981,497 A | 11/1999 | Maingault |

(Continued)

FOREIGN PATENT DOCUMENTS

| CN | 105 087 173 | 11/2015 |
| CN | 105661630 A | 6/2016 |

(Continued)

OTHER PUBLICATIONS

Abdel-Mawgoud et al., "Rhamnolipids: Diversity of Structures, Microbial Origins and Roles," Applied Microbiology and Biotechnology, Springer, Berlin, DE, copyright Mar. 2010, vol. 86, No. 5, pp. 1323-1336 (14 pages).

(Continued)

*Primary Examiner* — Helen F Heggestad
(74) *Attorney, Agent, or Firm* — Taylor English Duma LLP; Philip P. McCann

(57) ABSTRACT

The invention relates to compositions comprising glycolipids and benzoic acid and/or sorbic acid.

20 Claims, 2 Drawing Sheets

(51) Int. Cl.

| | |
|---|---|
| A23L 3/349 | (2006.01) |
| A23L 3/3544 | (2006.01) |
| A23L 27/00 | (2016.01) |
| A61K 8/368 | (2006.01) |
| A61Q 11/00 | (2006.01) |
| A01N 43/16 | (2006.01) |
| A61Q 19/00 | (2006.01) |
| A23L 29/00 | (2016.01) |
| A61K 8/36 | (2006.01) |
| A61K 8/60 | (2006.01) |
| A61Q 5/02 | (2006.01) |
| A61Q 1/14 | (2006.01) |
| A61Q 19/10 | (2006.01) |
| A23L 3/3508 | (2006.01) |

(52) U.S. Cl.
CPC ............ *A23L 3/3508* (2013.01); *A23L 3/3544* (2013.01); *A23L 27/86* (2016.08); *A23L 29/03* (2016.08); *A61K 8/36* (2013.01); *A61K 8/368* (2013.01); *A61K 8/602* (2013.01); *A61Q 1/14* (2013.01); *A61Q 5/02* (2013.01); *A61Q 11/00* (2013.01); *A61Q 19/00* (2013.01); *A61Q 19/10* (2013.01); *A23V 2002/00* (2013.01); *A23V 2200/10* (2013.01); *A61K 2800/10* (2013.01); *A61K 2800/524* (2013.01)

(58) Field of Classification Search
USPC .................................................. 426/335, 601
See application file for complete search history.

(56) References Cited

U.S. PATENT DOCUMENTS

| | | |
|---|---|---|
| 8,911,982 B2 | 12/2014 | Schaffer et al. |
| 9,068,211 B2 | 6/2015 | Schaffer et al. |
| 9,085,787 B2 | 7/2015 | Schaffer et al. |
| 9,102,968 B2 | 8/2015 | Schaffer et al. |
| 9,157,108 B2 | 10/2015 | Schaffer et al. |
| 9,243,212 B2 | 1/2016 | Kuppert et al. |
| 9,271,908 B2 | 3/2016 | Allef et al. |
| 9,351,485 B2 | 5/2016 | Giessler-Blank et al. |
| 9,434,755 B2 | 9/2016 | Schilling et al. |
| 2012/0145956 A1 | 6/2012 | Walden et al. |
| 2014/0178444 A1* | 6/2014 | Stadler et al. |
| 2014/0296168 A1* | 10/2014 | Schilling et al. |
| 2016/0249604 A1 | 9/2016 | Giessler-Blank et al. |
| 2017/0218120 A1 | 8/2017 | Brandt et al. |
| 2017/0306264 A1 | 10/2017 | Peggau et al. |
| 2017/0335238 A1 | 11/2017 | Schilling et al. |
| 2018/0016525 A1 | 1/2018 | Scheuermann et al. |
| 2018/0023040 A1 | 1/2018 | Schilling et al. |
| 2018/0344602 A1 | 12/2018 | Schuch et al. |
| 2019/0040095 A1 | 2/2019 | Lu et al. |

FOREIGN PATENT DOCUMENTS

| | | |
|---|---|---|
| EP | 1 411 111 B1 | 9/2008 |
| EP | 2501813 A2 | 9/2012 |
| EP | 2 532 232 A1 | 12/2012 |
| EP | 2 786 742 A1 | 10/2014 |
| WO | 2011/061032 A2 | 5/2011 |
| WO | 2017/144317 A1 | 8/2017 |
| WO | 2018/065314 A1 | 4/2018 |
| WO | 2018/145966 A1 | 8/2018 |
| WO | 2019/038125 A1 | 2/2019 |

OTHER PUBLICATIONS

Cortés-Sánchez et al., "Biological Activity of Glycolipids Produced By Microorganisms: New Trends and Possible Therapeutic Alternatives," Microbiological Research, copyright Jan. 2013, vol. 168, No. 1, pp. 22-32 (22 pages).

German language Written Opinion dated Nov. 15, 2017 in PCT/EP2017/074795 (8 pages).

International Search Report dated Nov. 15, 2017 in PCT/EP2017/074795 (4 pages).

Kapjung et al., "Characteristics of Sophorolipid as an Antimicrobial Agent," Journal of Microbiology and Biotechnology, Korean Society for Applied Microbiology, Seoul, KR, copyright Jan. 2002, vol. 12, No. 2, pp. 235-241 (7 pages).

Klostermann et al., U.S. Appl. No. 16/315,744, filed Jan. 7, 2019.

Liebig et al., U.S. Appl. No. 16/312,480, filed Dec. 21, 2018.

* cited by examiner

COMPOSITION CONTAINING GLYCOLIPIDS AND PRESERVATIVES

CROSS REFERENCE TO RELATED APPLICATION

This application is a 35 U.S.C. § 371 U.S. national phase entry of International Application No. PCT/EP2017/074795 having an international filing date of Sep. 29, 2017, which claims the benefit of EP Application No. 16192743.9 filed Oct. 7, 2016, each of which is incorporated herein by reference in its entirety.

FIELD

The invention relates to compositions comprising glycolipids and benzoic acid and/or sorbic acid.

BACKGROUND

Preservatives are used to protect a wide variety of products from microbial contamination and spoilage. In recent years, a series of preservatives have fallen into disrepute due to toxicological concerns and their use has been partly limited by law. Preservatives which have not been affected in this regard have other disadvantages however, for example they are only effective over a limited pH range or they are not effective over the whole spectrum of microorganisms. In this regard, it has become increasingly difficult to provide safe preservation of, for example, foodstuffs, cosmetics and other products, and there is a demand for products which are effective and usable in a variety of ways.

Benzoic acid and sorbic acid and salts thereof belong to the group of preservatives still approved for many applications and established as of no toxicological concern. However, these have the disadvantage that they only have sufficient efficacy in protonated form in the acidic range. A significant effect is obtained in a practically relevant concentration range only at pH<5.5. Furthermore, they have an unpleasant burning taste (Otero-Losada, M. 1999—*Kinetic study on benzoic acid pungency*) such that their usable concentration and therefore their efficacy in foodstuffs and dental care products is limited.

Glycolipids are lipids glycosidically linked to sugars. This compound class includes also the rhamnolipids (RL) and sophorolipids (SL) known as biosurfactants which may be produced, for example, by microbial fermentation. An antimicrobial effect is described but this is limited to certain organisms, in particular gram-positive bacteria. For example, no antimicrobial effect of rhamnolipids could be detected on *Eschericia coli* NCTC 10418 and *Pseudomonas aeruginosa* PAO1, while *Bacillus subtilis* NCTC 10400 was inhibited. (Diaz De Reinzo, M. A., Stevenson, P., Marchant, R., Banat, I. M. (2016) *Antimicrobial properties of biosurfactants on selected Gram-positive and-negative bacteria*. FEMS Microbiology Letters, 363, 1-8). Good efficacy could be shown for sophorolipids on various gram-positive bacteria but not on *E. coli* (Kapjung, K. et al. *Characteristics of Sophorolipid as an Antimicrobial Agent*, Journal of Microbiology and Biotechnology, Volume 12, Issue 2, 2002, pp. 235-241). The taste profile of these glycolipids is not known.

The object of the invention was to increase the antimicrobial efficacy of benzoic acid and sorbic acid and salts thereof in the pH range >5.5 and at the same time to reduce the unpleasant taste impression of these preservatives.

SUMMARY

It has now been found, surprisingly, that the addition of glycolipids to benzoic acid and/or sorbic acid substantially neutralizes the unpleasant taste of these acids. In addition, the pH range in which these preservatives are effective could be extended. Whereas neither benzoic acid/sorbic acid nor glycolipids showed sufficiently preserving effect at the concentration used, the mixture resulted in good stabilization with respect to microbial growth.

The invention relates to compositions comprising benzoic acid and/or sorbic acid and glycolipids.

DETAILED DESCRIPTION OF THE INVENTION

Figure 1:
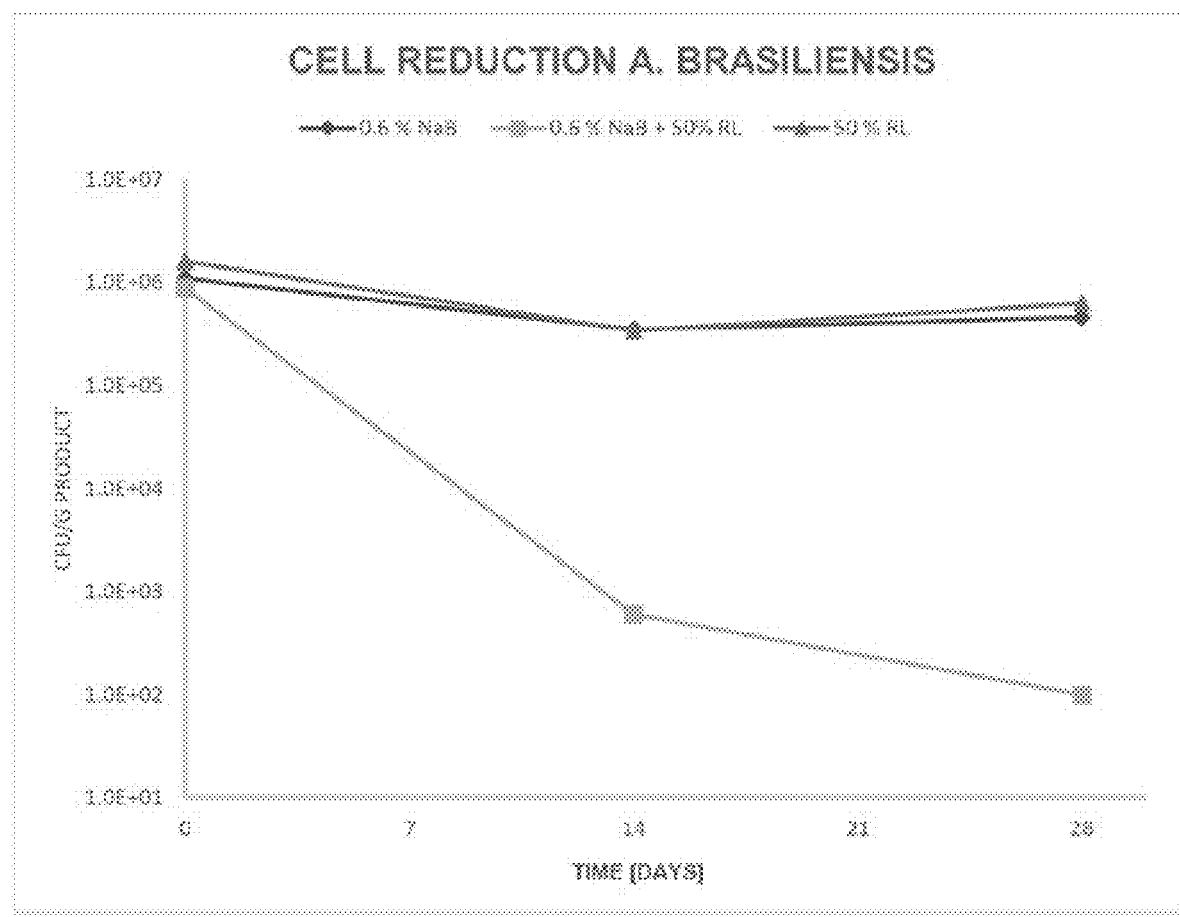
FIG. 1 shows a graft of the cell reduction of *Aspergillus brasiliensis*.

An advantage of the present invention is that these preservatives may be used in the corresponding mixtures in a relatively broad pH range and product range. For example, they may be used for improving taste and for microbiological stabilization of dental care products such as mouthwashes and toothpastes but also for the stabilization and for improving the taste of care products (bath additives, lipstick etc.). A further advantage is that less perfume or flavour has to be used thereby in order to mask the unpleasant taste.

A further advantage is that products may also be preserved thereby which are unstable in a lower pH range. Yet another advantage is that the amount of preservative required can be reduced.

Compositions are claimed comprising 5% by weight to 70% by weight, preferably 6% by weight to 60% by weight, particularly preferably 10% by weight to 55% by weight and especially preferably 20% by weight to 50% by weight, of at least one glycolipid preferably selected from the group of rhamnolipids and sophorolipids, particularly rhamnolipids, and 0.1% by weight to 10% by weight, preferably 0.2% by weight to 5% by weight, particularly preferably 0.4% by weight to 1% by weight, of at least one preservative selected from the group consisting of sorbic acid, benzoic acid and salts of the aforementioned acids, where the percentages by weight refer to the total composition, characterized in that the pH of the composition at 25° C. is in a range from 3.5 to 9, preferably from 5.6 to 7, particularly preferably from 5.6 to 6.6.

Preferred compositions according to the invention comprise a glycolipid selected from the group of rhamnolipids and sophorolipids, in particular rhamnolipids.

The term "rhamnolipid" in the context of the present invention encompasses rhamnolipids, protonated forms thereof and also in particular salts thereof.

The term "rhamnolipid" in the context of the present invention is understood to mean particularly mixtures of compounds of the general formula (I) and salts thereof,

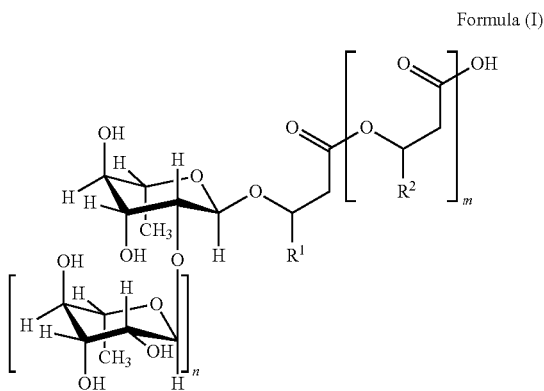

Formula (I)

where
m=2, 1 or 0,
n=1 or 0,
$R^1$ and $R^2$=mutually independently, identical or different, organic radical having 2 to 24, preferably 5 to 13 carbon atoms, in particular optionally branched, optionally substituted, particularly hydroxy-substituted, optionally unsaturated, in particular optionally mono-, bi- or tri-unsaturated alkyl radical, preferably that selected from the group consisting of pentenyl, heptenyl, nonenyl, undecenyl and tridecenyl and $(CH_2)_o$—$CH_3$ where o=1 to 23, preferably 4 to 12.

If n=1, the glycosidic bond between the two rhamnose units is preferably in the α-configuration. The optically active carbon atoms of the fatty acids are preferably present as R-enantiomers (e.g. (R)-3-{(R)-3-[2-O-(α-L-rhamnopyranosyl)-α-L-rhamnopyranosyl] oxydecanoyl}oxydecanoate).

The term "di-rhamnolipid" in the context of the present invention is understood to mean compounds of the general formula (I) or salts thereof, where n=1.

The term "mono-rhamnolipid" in the context of the present invention is understood to mean compounds of the general formula (I) or salts thereof, where n=0.

Distinct rhamnolipids are abbreviated according to the following nomenclature: "diRL-CXCY" is understood to mean di-rhamnolipids of the general formula (I), in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

"monoRL-CXCY" is understood to mean mono-rhamnolipids of the general formula (I), in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

The nomenclature used therefore does not differ between "CXCY" and "CYCX".

For rhamnolipids where m=0, monoRL-CX or diRL-CX is used accordingly.

If one of the abovementioned indices X and/or Y is provided with ":Z", this signifies that the respective radical $R^1$ and/or $R^2$=an unbranched, unsubstituted hydrocarbon radical having X-3 or Y-3 carbon atoms having Z double bonds.

To determine the content of rhamnolipids in the context of the present invention, only the mass of the rhamnolipid anion is considered, i.e. "general formula (I) less one hydrogen".

To determine the content of rhamnolipids in the context of the present invention, all rhamnolipids are converted by acidification into the protonated form (cf. general formula (I)) and quantified by HPLC.

Sophorolipids may be used in accordance with the invention in their acid form or their lactone form. With regard to the term "acid form" of sophorolipids reference is made to the general formula (Ia) of EP2501813, and with regard to the term "lactone form" of sophorolipids reference is made to the general formula (Ib) of EP2501813.

To determine the content of sophorolipids in the acid or lactone form in a composition, refer to EP 1 411 111 B1, page 8, paragraph [0053].

The "pH" in connection with the present invention is defined as the value which is measured for the relevant composition at 25° C. after stirring for five minutes using a pH electrode calibrated in accordance with ISO 4319 (1977).

The term "preservative" in the context of the present invention is understood to mean an agent which preserves with regard to microbial, particularly bacterial, growth.

Unless stated otherwise, all percentages (%) given are percentages by mass.

Benzoic acid is shown in formula (II) and sorbic acid in formula (III).

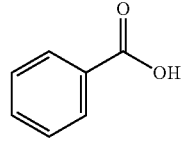

Formula (II)

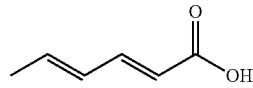

Formula (III)

It is possible to use in particular sodium, potassium or calcium salts but generally also other salts of these acids.

It is preferable in accordance with the invention that the ratio by weight of the glycolipids present in the composition according to the invention, preferably selected from the group of rhamnolipids and sophorolipids, particularly rhamnolipids, to the preservatives present, selected from the group consisting of sorbic acid, benzoic acid and salts of the aforementioned acids, is in a range from 1000:1 to 1:1, preferably from 500:1 to 10:1, particularly preferably from 100:1 to 30:1.

In addition to these preservatives, further preservatives may be present to increase the effect. For example, at least one further preservative selected from the group of isothiazolinones may be added. Furthermore, at least one further preservative may be present selected from the group consisting of phenoxyethanol, benzyl alcohol, parabens, antimicrobial peptides (e.g. nisin, natamycin), terpenes (e.g. limonene or perillic acid), antimicrobial fatty acids (e.g. caprylic acid), formaldehyde releasers (DMDM hydantoin) and alcohols (e.g. ethanol).

The glycolipids present in the compositions according to the invention may be present at least partially as salts on account of the given pH.

In compositions preferred according to the invention the cations of the glycolipid salts present are selected from the group comprising, preferably consisting of, $Li^+$, $Na^+$, $K^+$, $Mg^{2+}$, $Ca^{2+}$, $Al^{3+}$, $NH_4^+$, primary ammonium ions, secondary ammonium ions, tertiary ammonium ions and quaternary ammonium ions.

Exemplary representatives of suitable ammonium ions are tetramethylammonium, tetraethylammonium, tetrapropylammonium, tetrabutylammonium and [(2-hydroxyethyl)

trimethylammonium] (choline) and also the cations of 2-aminoethanol (ethanolamine, MEA), diethanolamine (DEA), 2,2',2''-nitrilotriethanol (triethanolamine, TEA), 1-aminopropan-2-ol (monoisopropanolamine), ethylenediamine, diethylenetriamine, triethylenetetramine, tetraethylenepentamine, 1,4-diethylenediamine (piperazine), aminoethylpiperazine and aminoethylethanolamine.

Mixtures of the abovementioned cations may also be present according to the invention as cations of the glycolipid salts present.

Particularly preferred cations are selected from the group comprising, preferably consisting of, $Na^+$, $K^+$, $NH_4^+$ and the triethanolammonium cation.

The total amount of the abovementioned cations preferably accounts for 50% by weight to 99% by weight, particularly preferably 70% by weight to 90% by weight, of all cations present in the composition except $H^+$ and $H_3O^+$.

Preferred compositions according to the invention comprise 50% by weight to 99% by weight, preferably 70% by weight to 95% by weight, particularly preferably 85% by weight to 90% by weight, of glycolipid anions, preferably selected from the group of rhamnolipid anions and sophorolipid anions, especially rhamnolipid anions, where % by weight refers to all anions present in the composition except $OH^-$.

In particularly preferred compositions according to the invention, the total dry mass comprises 40% by weight to 98% by weight, preferably 50% by weight to 95% by weight, particularly preferably 60% by weight to 90% by weight, of glycolipids, preferably selected from the group of rhamnolipids and sophorolipids, particularly rhamnolipids, where the percentages by weight refer to the total dry mass.

In compositions preferred according to the invention, at least 60% by weight, preferably at least 80% by weight, particularly preferably at least 95% by weight, of the glycolipids, preferably selected from the group of rhamnolipids and sophorolipids, particularly rhamnolipids, are present in dissolved form, wherein the percentages by weight refer to the total amount of glycolipids, preferably selected from the group of rhamnolipids and sophorolipids, particularly rhamnolipids. This is measured by HPLC analysis of the total glycolipid before and after filtration through a 0.2 μm syringe filter, where the amount of glycolipids in the eluate corresponds to the amount of dissolved glycolipids.

It is preferred according to the invention that the compositions comprise 51% by weight to 95% by weight, preferably 70% by weight to 90% by weight, particularly preferably 75% by weight to 85% by weight, of diRL-C10C10, where the percentages by weight refer to the sum total of all rhamnolipids present.

It is preferred according to the invention that the compositions comprise 0.5% by weight to 9% by weight, preferably 0.5% by weight to 3% by weight, particularly preferably 0.5% by weight to 2% by weight, of monoRL-C10C10, where the percentages by weight refer to the sum total of all rhamnolipids present.

Preferred compositions according to the invention are characterized in that the ratio by weight of all di-rhamnolipids present to all mono-rhamnolipids present is greater than 51:49, particularly greater than 91:9, preferably greater than 97:3, particularly preferably greater than 98:2.

It is preferred according to the invention that the compositions comprise 0.5 to 25% by weight, preferably 5% by weight to 15% by weight, particularly preferably 7% by weight to 12% by weight, of diRL-C10C12, where the percentages by weight refer to the sum total of all rhamnolipids present.

It is preferred according to the invention that the compositions comprise 0.1% by weight to 5% by weight, preferably 0.5% by weight to 3% by weight, particularly preferably 0.5% by weight to 2% by weight, of monoRL-C10C12 and/or, preferably and, 0.1% by weight to 5% by weight, preferably 0.5% by weight to 3% by weight, particularly preferably 0.5% by weight to 2% by weight, of monoRL-C10C12:1, where the percentages by weight refer to the sum total of all rhamnolipids present.

Particularly preferred compositions according to the invention are characterized in that they comprise 0.5% by weight to 15% by weight, preferably 3% by weight to 12% by weight, particularly preferably 5% by weight to 10% by weight, of diRL-C10C12:1, 0.5 to 25% by weight, preferably 5% by weight to 15% by weight, particularly preferably 7% by weight to 12% by weight, of diRL-C10C12, 0.1% by weight to 5% by weight, preferably 0.5% by weight to 3% by weight, particularly preferably 0.5% by weight to 2% by weight, of monoRL-C10C12 and 0.1% by weight to 5% by weight, preferably 0.5% by weight to 3% by weight, particularly preferably 0.5% by weight to 2% by weight, of monoRL-C10C12:1, where the percentages by weight refer to the sum total of all rhamnolipids present.

It is moreover preferred if the composition according to the invention comprises only small amounts of rhamnolipids of the formula monoRL-CX or diRL-CX. In particular, the composition according to the invention preferably comprises 0% by weight to 5% by weight, preferably 0% by weight to 3% by weight, particularly preferably 0.1% by weight to 1% by weight, of diRLC10, where the percentages by weight refer to the sum total of all rhamnolipids present, and the term "0% by weight" is understood to mean no detectable amount.

It is preferred according to the invention that the compositions in accordance with the invention are essentially free from fatty oil (acylglycerols liquid at 20° C.) and therefore particularly comprise less than 0.5% by weight, in particular less than 0.1% by weight, particularly preferably no detectable amounts, of fatty oil based on the total composition.

Preferred compositions according to the invention comprise a sophorolipid as glycolipid in which the ratio by weight of lactone form to acid form is in the range of 20:80 to 80:20, especially preferably in the ranges of 30:70 to 40:60.

The present invention further relates to the use of glycolipids, preferably selected from sophorolipids and rhamnolipids, particularly rhamnolipids, to improve the antimicrobially, particularly bacterially, preserving effect of the preservatives selected from the group consisting of sorbic acid, benzoic acid and salts of the aforementioned acids.

The present invention further relates to the use of glycolipids, preferably selected from sophorolipids and rhamnolipids, particularly rhamnolipids, to reduce the bitter taste of the preservatives selected from the group consisting of sorbic acid, benzoic acid and salts of the aforementioned acids.

The present invention also relates to the use of the compositions according to the invention as preservatives for foodstuffs, cosmetic products, household cleaners, washing and rinsing agents, dental care products and medicinal products, especially for foodstuffs and dental care products.

The examples adduced hereinafter describe the present invention by way of example, without any intention that the invention, the scope of application of which is apparent from the entirety of the description and the claims, be restricted to the embodiments specified in the examples.

EXAMPLES

Example 1: Taste Masking of Benzoic Acid and Sorbic Acid by Addition of Rhamnolipids Rhamnolipids partially neutralized with KOH were prepared as described in EP3023431A1 (concentrated low-viscosity rhamnolipid compositions) and analysed. A rhamnolipid solution was obtained with a dry mass content of 40% and a pH of 6. The proportion of rhamnolipids and salts thereof was >90% by weight based on the dry mass. The relative proportions of the various rhamnolipid congeners in percent by weight of the sum total of all rhamnolipids are given in the following table. Here, the ratios refer to the acid form which is quantified in the HPLC analysis.

TABLE 1

Composition of the rhamnolipids used. Data in % by weight of the respective congener (as acid form) based on the sum total of all rhamnolipids (as acid form).

| | |
|---|---|
| diRL-C8C10 | 15.8 |
| diRL-C10C10 | 66.4 |
| diRL-C10C12:1 | 6.4 |
| diRL-C10C12 | 6.2 |
| monoRL-C10C10 | 2.4 |
| other rhamnolipids | 2.8 |

The protein content was determined by the photometric bicinchoninic assay (BCA assay, ThermaFisher Scientific) and was <1% by weight based on the dry mass of the rhamnolipid.

The highly concentrated rhamnolipid solution obtained was diluted and sodium benzoate or sodium sorbate (Sigma Aldrich) was added. Solutions with the compositions described in the table below were prepared. The solutions were adjusted to pH=6.

TABLE 2

Compositions for sensory evaluation (data in % by weight, residual water)

| | M1 | M2 | M3 | M4 | M5 | M6 |
|---|---|---|---|---|---|---|
| Potassium sorbate | 0.5 | 0.5 | 0.5 | | | |
| Potassium benzoate | | | | 0.5 | 0.5 | 0.5 |
| Rhamnolipids | | 10 | | | 10 | |
| Sorbitol | | | 10 | | | 10 |

The sensory evaluation of the mixtures was then carried out. For this purpose, 5 ml each were tasted by a panel (10 participants) and the taste impression described. For the sorbic acid or benzoic acid without additives, an unpleasant, burning and slightly astringent taste was described which could not be concealed by addition of sorbitol. In the presence of the rhamnolipids, this taste impression was barely perceived, rather only a slightly sweet, coconut-like taste was described.

Example 2: Synergistic Effect of Rhamnolipids and Benzoic Acid or Sorbic Acid

By addition of potassium benzoate and/or potassium sorbate to the highly concentrated rhamnolipid solution described in example 1, the compositions described in the following table were prepared and the pH was adjusted to 5.8.

TABLE 3

Compositions for microbial contamination tests (data in % by weight, residual water)

| | M7 | M8 | M9 | M10 | M11 | M12 | M13 |
|---|---|---|---|---|---|---|---|
| Potassium benzoate | 0.6 | 0.6 | | | | 0.6 | 0.6 |
| Potassium sorbate | | | 0.6 | 0.6 | | 0.6 | 0.6 |
| Rhamnolipids | | 40 | | 40 | 40 | | 40 |

Microbial contamination tests were then conducted according to the European Pharmacopoeia 7th edition 2011, paragraph 5.1.3. For this purpose, the compositions in table 3 were inoculated with a defined germ count of various microorganisms and the inoculated samples stored at room temperature. At fixed time points, the germ count was measured. The microorganisms used for the microbial contamination tests were *Escherichia coli, Pseudomonas aeruginosa, Staphylococcus aureus, Candida albicans* and *Aspergillus brasiliensis*.

Potassium benzoate (M7) had practically no effect at this pH and the germ count was not reduced. Potassium sorbate (M9) had only a small effect. Also the combination of potassium benzoate and potassium sorbate (M12) or rhamnolipids alone (M11) had only a small effect. In particular, the germ count of yeasts and fungi was not significantly reduced. The combination of potassium sorbate (M10), of potassium benzoate (M8) or mixtures thereof (M13) with rhamnolipids, however, afforded a very good reduction of all microorganisms investigated. The gram-bacteria and yeasts in particular could be reduced significantly more rapidly and even after 2 days (first test time point) living microbes could no longer be detected.

Example 2b: Synergistic Effect of Rhamnolipids and Benzoic Acid

The compositions described in the following table were prepared by adding sodium benzoate to the highly concentrated rhamnolipid solution described in Example 1 and the pH was adjusted to 5.8.

TABLE 4

Compositions for microbial contamination tests (data in % by weight, residual water)

| | M14 | M15 | M16 |
|---|---|---|---|
| Sodium benzoate | 0.6 | | 0.6 |
| Rhamnolipids | | 50 | 50 |

Microbial contamination tests were then conducted according to the European Pharmacopoeia 7th edition 2011, paragraph 5.1.3. For this purpose, the compositions in table 4 were inoculated with a defined germ count of various microorganisms and the inoculated samples stored at room temperature. At fixed time points, the germ count was measured.

The microorganisms used for the microbial contamination tests were *Candida albicans* and *Aspergillus brasiliensis*.

Figure 2:
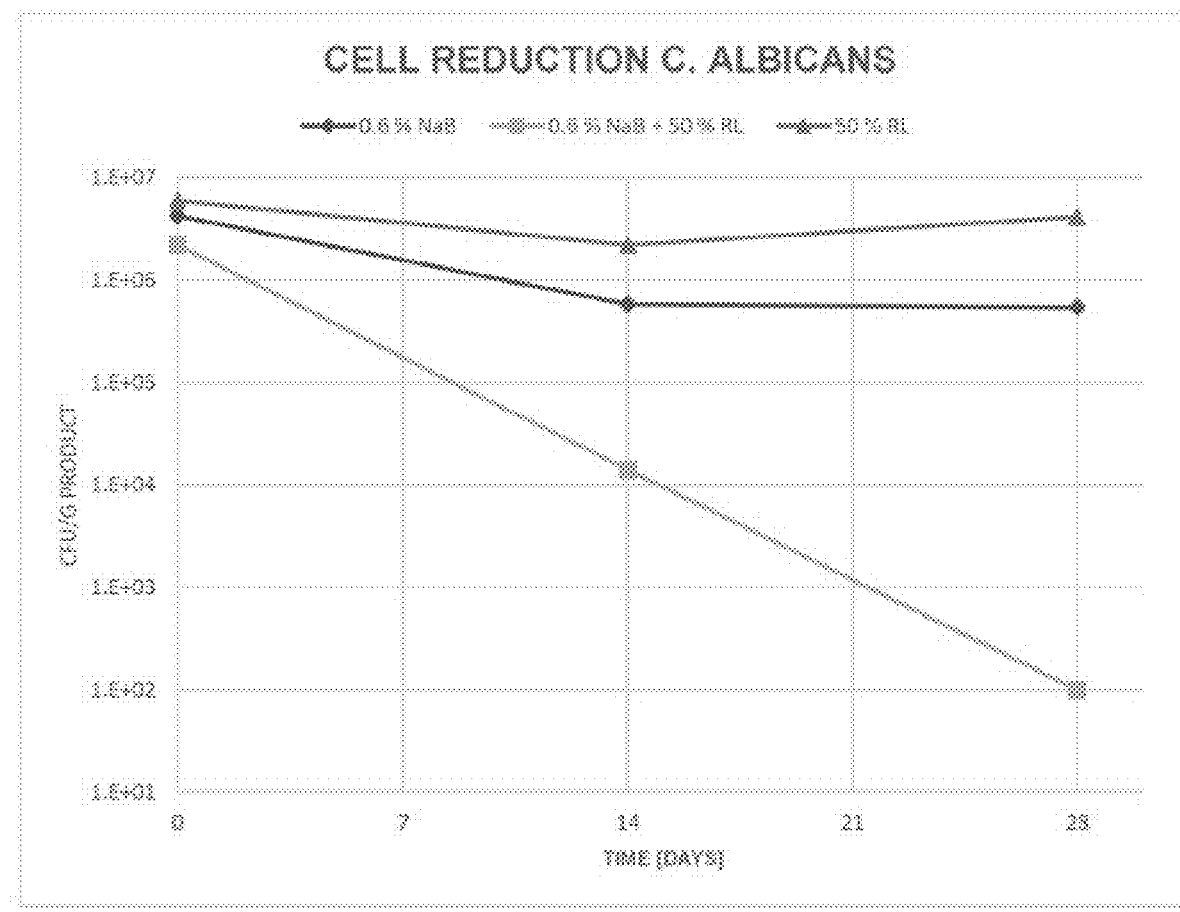
FIG. 2 shows a graft of the cell reduction *Candida albicans*.

The results are presented in FIGS. 1 and 2 and show a synergistic effect of the two components.

Example 3: Synergistic Effect of Sophorolipids with a Mixture of Benzoic Acid and Sorbic Acid A commercial sophorolipid (Rewoferm® SL446) was diluted to a sophorolipid content of 10%. 0.1% sorbic acid and 0.1% benzoic acid were added to a sample and a further sample was not preserved. The pH of both samples was adjusted to 6.2. An aqueous solution of 0.1% sorbic acid and 0.1% benzoic acid was also prepared and the pH adjusted to 6.2. The three samples were then subjected to a microbial contamination test with *Aspergillus brasiliensis* as described in example 2. Only in the combination of sophorolipid with preservatives was a significant germ count reduction observed over time.

Example 4: Synergistic Effect of Rhamnolipids with a Mixture of Benzoic Acid and Sorbic Acid In the present case, the minimum inhibitory concentrations were determined for various compositions with respect to *Candida albicans* according to the microdilution method based on *Candida albicans* DSM1386 from the primary culture was inoculated on a Sab. agar plate and incubated at 30° C. for 2 days. From this preculture, a Sab. agar slant tube was inoculated and in turn incubated at 30° C. for two days.

To prepare the test inoculum, the agar slant tubes were rinsed with seven ml of Mueller-Hinton broth pH 6, the microbial suspensions rinsed off were filled into 100 ml flasks containing 5 g of glass beads and the flasks placed on an orbital shaker for 3 minutes.

These microbial suspensions were diluted 1:100 in order to achieve a germ count of $10^6$ CFU/ml in the test inoculum.

The exact germ count of the inoculum was determined with the aid of a spiralometer. Appropriate dilution sequences of 100 µl aliquots of the substances to be tested in Mueller-Hinton broth were placed in a microtitre plate and provided with 100 µl of the *Candida albicans* culture prepared above and the plate was incubated at 30° C. for two to three days.

On the basis of the absence or presence of cell growth at the respective test substance concentration, the minimum inhibitory concentration was determined.

A 2:1 mixture based on weight of sodium benzoate to potassium sorbate exhibited a minimum inhibitory concentration of 0.5 to 1% in the experimental set-up, whereas proceeding from the rhamnolipids of Example 1 at the highest concentration used of 10%, no inhibition was observable.

For a 2:1:130 mixture based on weight of sodium benzoate to potassium sorbate to rhamnolipid, the minimum inhibitory concentration (MIC) was reduced to 0.5 (based on sodium benzoate and potassium sorbate) and 10 (based on rhamnolipid) respectively:

| Na benzoate [%] | K sorbate [%] | RL [%] | MIC |
|---|---|---|---|
| — | — | 20 | —/>10 |
| 4.8 | 2.4 | — | 0.5-1/— |
| 0.3 | 0.15 | 20 | 0.5/10 |

Further Formulation Examples

| Mouthwash, pH = 6 (data in % by weight) | |
|---|---|
| Rhamnolipid, 40% by weight in water, pH = 6 | 18.0 |
| Sorbitol | 3.0 |
| Ethyl alcohol | 5.0 |
| Benzoic acid | 0.1 |
| Aroma | 0.2 |
| Aqua, demin. | to 100 |

| Shampoo (data in % by weight) | |
|---|---|
| Rhamnolipid | 9.0 |
| TEGO ® Betaine P 50 C, 38% (INCI: Cocamidopropyl Betaine) | 7.9 |
| VARISOFT ® EQ 100 (INCI: Bis(Isostearoyl/Oleyl Isopropyl) Dimonium Methosulfate) | 1.0 |
| Guar Hydroxypropyl Trimonium Chloride | 0.2 |
| Xanthan Gum | 1.0 |
| Benzoic acid | 0.1 |
| Sorbic acid | 0.1 |
| Citric acid | to pH 5.8 |
| Perfume, dyes | q.s. |
| Aqua, demin. | to 100 |

| Shampoo (data in % by weight) | |
|---|---|
| Rewoferm ® SL 446 (Sophorolipid) | 18.0 |
| TEGO ® Betaine P 50 C, 38% (INCI: Cocamidopropyl Betaine) | 3.2 |
| REWOTERIC ® AM C, 32% (INCI: Sodium Cocoamphoacetate) | 15.0 |
| REWOPOL ® SB F 12 P (INCI: Disodium Lauryl Sulfosuccinate) | 3.6 |
| ABIL ® ME 45, 30% (INCI: Silicone Quaternium-22; Polyglyceryl-3 Caprate; Dipropylene Glycol; Cocamidopropyl Betaine) | 3.3 |
| Guar Hydroxypropyl Trimonium Chloride | 0.2 |
| Xanthan Gum | 0.5 |
| Benzoic acid | 0.1 |
| Sorbic acid | 0.05 |
| Citric acid | to pH 5.8 |
| Perfume, dyes | q.s. |
| Aqua, demin. | to 100 |

| Shower cream (data in % by weight) | |
|---|---|
| Rhamnolipid | 9.0 |
| Hydroxypropyl Starch Phosphate, 100% | 5.0 |
| TEGO ® Betaine P 50 C, 38% (INCI: Cocamidopropyl Betaine) | 18.40 |
| Myristic Acid | 4.0 |
| Soybean Oil | 2.9 |
| NaCl | 2.6 |
| Benzoic acid | 0.15 |
| Sorbic acid | 0.1 |
| Citric acid | to pH 6.0 |
| Perfume, dyes | q.s. |
| Aqua, demin. | to 100 |

| Make-up remover (data in % by weight) | |
|---|---|
| Rhamnolipid, 50% by weight in water | 15 |
| Rewoferm SL 446 (Sophorolipid) | 15 |
| TEGOSOFT ®PC 41 (INCI: Polyglyceryl-4 Caprate) | 1.0 |

-continued

| Make-up remover (data in % by weight) | |
|---|---|
| TEGO ® Solve 61 (INCI: Polyglyceryl-6 Caprylate; Polyglyceryl-3 Cocoate; Polyglyceryl-4 Caprate; Polyglyceryl-6 Ricinoleate) | 1.0 |
| TEGO ® Natural Betaine (INCI: Betaine) | 1.0 |
| Hexylene Glycol | 1.4 |
| Glycerol | 1.0 |
| Water | to 100 |
| Benzoic acid | 0.1 |
| Sorbic acid | 0.1 |
| Citric acid | to pH 5.6 |
| Perfume, dyes | q.s. |
| Aqua, demin. | to 100 |

The invention claimed is:

1. A composition comprising
   from 5% by weight to 70% by weight of at least one glycolipid selected from the group consisting of rhamnolipids and sophorolipids wherein the at least one glycolipid comprise from 50 to 99% by weight of salts comprising cations selected from the group consisting of $Li^+$, $Na^+$, $K^+$, $Mg^{2+}$, $Ca^{2+}$, $Al^{3+}$, $NH_4^+$, primary ammonium ions, secondary ammonium ions, tertiary ammonium ions and quaternary ammonium ions of all cations present in the composition except $H^+$ and $H_3O^+$,
   from 0.1% by weight to 10% by weight of at least one preservative selected from the group consisting of sorbic acid, benzoic acid and salts of the aforementioned acids, and
   an isothiazolinone,
   where the percentages by weight refer to the total composition, wherein the pH of the composition at 25° C. is in a range from 3.5 to 9, and the ratio by weight of the glycolipids to the at least one preservative is in a range from 1000:1 to 10:1.

2. The composition according to claim 1, wherein
   the ratio by weight of the at least one glycolipid to the at least one preservative is in a range from 500:1 to 1:1, and the at least one glycolipid comprise from 70 to 90% by weight of salts.

3. The composition according to claim 1, further comprising
   at least one further preservative selected from the group consisting of isothiazolinones, phenoxyethanol, benzyl alcohol, parabens, antimicrobial peptides, terpenes, antimicrobial fatty acids, formaldehyde releasers and alcohols.

4. The composition according to claim 1, wherein said glycolipid is a rhamnolipid, and said composition comprises
   from 51% by weight to 95% by weight of diRL-C10C10,
   where the percentages by weight refer to the sum total of the rhamnolipid.

5. The composition according to claim 1, wherein said glycolipid is a rhamnolipid, and said composition comprises
   from 0.5% by weight to 9% by weight of monoRL-C10C10,
   where the percentages by weight refer to the sum total of the rhamnolipid.

6. The composition according to claim 1, wherein said glycolipid comprises mono-rhamnolipid and di-rhamnolipid, and the ratio by weight of the di-rhamnolipid to the mono-rhamnolipid is greater than 51:49.

7. The composition according to claim 6, wherein the ratio by weight of the di-rhamnolipid to the mono-rhamnolipid is greater than 98:2.

8. The composition according to claim 1, wherein said glycolipid is a rhamnolipid, and said composition comprises
   0.5 to 25% by weight of diRL-C10C12,
   where the percentages by weight refer to the sum total of the rhamnolipid.

9. The composition according to claim 1, wherein said glycolipid is a rhamnolipid, and said composition comprises
   0.1% by weight to 5% by weight of monoRL-C10C12,
   where the percentages by weight refer to the sum total of all rhamnolipids present.

10. A cosmetic preservative comprising the composition of claim 1.

11. A foodstuff preservative comprising the composition of claim 1.

12. A dental care product preservative comprising the composition according to claim 1.

13. The composition according to claim 1 comprising
    from 6% by weight to 60% by weight of a rhamnolipid, and
    from 0.2% by weight to 5% by weight of at least one preservative selected from the group consisting of sorbic acid, benzoic acid and salts of the aforementioned acids,
    where the percentages by weight refer to the total composition,
    wherein the pH of the composition at 25° C. is in a range from 5.6 to 7.

14. The composition according to claim 1 comprising
    from 10% by weight to 55% by weight of a rhamnolipid, and
    from 0.4% by weight to 1% by weight of at least one preservative selected from the group consisting of sorbic acid, benzoic acid and salts of the aforementioned acids,
    where the percentages by weight refer to the total composition,
    wherein the pH of the composition at 25° C. is in a range from 5.6 to 6.6.

15. The composition according to claim 1 comprising
    from 20% by weight to 50% by weight of a rhamnolipid, and
    from 0.4% by weight to 1% by weight of at least one preservative selected from the group consisting of sorbic acid, benzoic acid and salts of the aforementioned acids,
    where the percentages by weight refer to the total composition,
    wherein the pH of the composition at 25° C. is in a range from 5.6 to 6.6.

16. The composition according to claim 1, wherein
    the ratio by weight of the glycolipids to the at least one preservative is in a range from 100:1 to 10:1.

17. The composition according to claim 1, wherein the ratio by weight of the glycolipids to the at least one preservative is in a range from 100:1 to 30:1.

18. The composition according to claim 1, wherein said glycolipid is a rhamnolipid, and the ratio by weight of the rhamnolipid to the at least one preservative is in a range from 1000:1 to 1:1.

19. The composition according to claim 1, wherein said glycolipid is a rhamnolipid, and said composition comprises
    0.1% by weight to 5% by weight of monoRL-C10C12:1,
    wherein the percentages by weight refer to the sum total of the rhamnolipid.

20. The composition according to claim 1, wherein said glycolipid is a rhamnolipid, and the ratio by weight of the rhamnolipid to the at least one preservative is in a range from 100:1 to 30:1.

* * * * *